United States Patent
Morgan et al.

(10) Patent No.: US 12,383,420 B2
(45) Date of Patent: Aug. 12, 2025

(54) MANDIBULAR ADVANCEMENT DEVICE WITH AUTOMATIC ADJUSTMENT MEANS

(71) Applicant: BIOANALYTICS HOLDINGS LIMITED, Victoria (AU)

(72) Inventors: Owen Morgan, New South Wales (AU); Anthony Sasse, Victoria (AU)

(73) Assignee: BIOANALYTICS HOLDINGS LIMITED, Melbourne (AU)

( * ) Notice: Subject to any disclaimer, the term of this patent is extended or adjusted under 35 U.S.C. 154(b) by 592 days.

(21) Appl. No.: 17/638,691

(22) PCT Filed: Aug. 26, 2020

(86) PCT No.: PCT/AU2020/000089
§ 371 (c)(1),
(2) Date: Feb. 25, 2022

(87) PCT Pub. No.: WO2021/035279
PCT Pub. Date: Mar. 4, 2021

(65) Prior Publication Data
US 2023/0023562 A1    Jan. 26, 2023

(30) Foreign Application Priority Data
Aug. 26, 2019   (AU) .................. 2019903108

(51) Int. Cl.
*A61F 5/56*  (2006.01)
*A61B 5/00*  (2006.01)
(Continued)

(52) U.S. Cl.
CPC .............. *A61F 5/566* (2013.01); *A61B 5/087* (2013.01); *A61B 5/097* (2013.01); *A61B 5/4836* (2013.01);
(Continued)

(58) Field of Classification Search
CPC ....... A61F 5/56–566; A61C 7/00; A61C 7/06; A61C 7/36; A61C 7/10; A61C 19/045;
(Continued)

(56) References Cited

U.S. PATENT DOCUMENTS 5,921,241 A   7/1999  Belfer
6,155,262 A   12/2000 Thornton et al.
(Continued)

FOREIGN PATENT DOCUMENTS

CN         109602534 A       4/2019
WO     WO-2006072147 A1 *   7/2006   ............. A61C 7/065
(Continued)

*Primary Examiner* — Michelle J Lee
(74) *Attorney, Agent, or Firm* — Bookoff McAndrews, PLLC (57) ABSTRACT

The present invention is an adjustment means for a mandibular advancement device. The mandibular advancement device being of the type having both intraoral and extraoral portions, including a body portion that is at the interface between the intraoral and extraoral portions and thereby is part intraoral and part extraoral. The extraoral portion includes a lower arm that is substantially straight and extends directly outwardly from the extraoral part of the body portion, and a curved upper arm that curves upwardly from the lower arm and back towards the face of a person using the device. The posterior end of the upper arm includes a pad assembly that is adapted to make contact with, and apply pressure to, the subnasal maxillary bone of the wearer. A substantial portion of the lower arm is engageable with motorised means that are encapsulated within the body portion and are adapted to engage with the lower arm and cause it to slide further out of, or slidably retract further into, the body portion.

12 Claims, 5 Drawing Sheets

(51) Int. Cl.
    *A61B 5/087*         (2006.01)
    *A61B 5/097*         (2006.01)
    *G16H 40/63*         (2018.01)

(52) U.S. Cl.
    CPC .......... *A61B 5/6819* (2013.01); *A61B 5/6835* (2013.01); *G16H 40/63* (2018.01); *A61B 2560/0271* (2013.01)

(58) Field of Classification Search
    CPC ........ A61C 19/04; G16H 40/60; G16H 40/63; A61B 5/08; A61B 5/087; A61B 5/097; A61B 5/48; A61B 5/4836; A61B 5/68; A61B 5/6801; A61B 5/6813; A61B 5/6819; A61B 5/6835; A61B 2560/02; A61B 2560/0266; A61B 2560/0271
    See application file for complete search history.

(56) References Cited

U.S. PATENT DOCUMENTS

| | | | |
|---|---|---|---|
| 6,877,513 B2 * | 4/2005 | Scarberry | ............... A61F 5/566 128/200.24 |
| 2016/0199215 A1 | 7/2016 | Kopelman | |
| 2017/0196727 A1 | 7/2017 | Giridharagopalan | |
| 2018/0147084 A1 | 5/2018 | Thornton et al. | |
| 2019/0167467 A1 | 6/2019 | Remmers et al. | |

FOREIGN PATENT DOCUMENTS

| | | | | |
|---|---|---|---|---|
| WO | WO 2018/111020 A1 | 6/2018 | | |
| WO | WO-2019071291 A1 * | 4/2019 | ........... | A61B 5/0004 |

* cited by examiner

MANDIBULAR ADVANCEMENT DEVICE WITH AUTOMATIC ADJUSTMENT MEANS

CROSS-REFERENCE TO RELATED APPLICATIONS

This application is the U.S. national phase entry under 35 U.S.C. § 371 of International Application No. PCT/AU2020/000089, filed on Aug. 26, 2020, which claims the benefit of priority of Australian Patent Application No. 2019903108, filed on Aug. 26, 2019.

FIELD OF THE INVENTION

This invention relates to mandibular advancement devices, particularly to devices worn by a person to prevent obstructive sleep apnoea, and in particular to motorised adjustment means that are either operated manually or autonomously, for the extraoral portion of that device.

BACKGROUND OF THE INVENTION

A mandibular advancement device of the type referred to in this specification is already disclosed in WO 2019/071291 A1 and WO 2006/072147. The mandibular advancement device disclosed has both intraoral and extraoral portions. The present invention is mainly concerned with the extraoral portion of the device.

The purpose of the device is to adjust the position of the mandible of the wearer so that their airway is clear to enable normal breathing. Typically, this type of device is worn at night while the wearer is sleeping. The device typically includes manual mechanical adjustment means that allow the wearer, or a care giver, to manually adjust the position of the mandible of the wearer. The problem with this is that once the position is selected, and the wearer goes to sleep, then the device keeps the mandible in that position during the entire sleep period. Unfortunately, what may have been the best position for the mandible at the commencement of sleep may not be the best position at other times during the sleep cycle. For example, if the breathing alters during the night, this indicates that the device may need adjusting. Often a partner, care giver, or the wearer themselves needs to intervene and make manual adjustments to the device. This is disruptive and non-conducive to a good night's sleep.

It is therefore an object of the present invention to provide automatic adjustment means for the extraoral portion of a mandibular advancement device that at least mitigates some of the aforementioned problems.

DISCLOSURE OF THE INVENTION

According to one form, the present invention is an adjustment means for a mandibular advancement device. The mandibular advancement device being of the type having both intraoral and extraoral portions, including a body portion that is at the interface between the intraoral and extraoral portions and thereby is part intraoral and part extraoral. The extraoral portion includes a lower arm that is substantially straight and extends directly outwardly from the extraoral part of the body portion, and a curved upper arm that curves upwardly from the lower arm and back towards the face of a person using the device. The posterior end of the upper arm includes a pad assembly that is adapted to make contact with, and apply pressure to, the subnasal maxillary bone of the wearer. A substantial portion of the lower arm is engageable with motorised means that are encapsulated within the body portion and are adapted to engage with the lower arm and cause it to slide further out of, or slidably retract further into, the body portion.

Preferably, the pad assembly includes sensor means that are adapted to sense the airflow emanating from the nose of the wearer as they breath while wearing the device and feed the sensor data collected in real time to logic control means contained within the body portion.

Preferably, the logic control means are adapted to process the sensor data it receives to determine if the position of the mandibular of the wearer needs adjusting to improve airflow from the wearer, and if so, then the logic control means are adapted to activate the motorised means to either extend or retract the lower arm for the appropriate distance, thereby causing the pad assembly to apply more or less pressure to the subnasal maxillary bone, and thereby change the position of the mandible of the wearer into the desired position.

Preferably, the device further includes manual means that are adapted to enable a user to manually control the motorised means so that the user can set a first desired position for the extraoral portion of the device.

Preferably, the manual means includes a switch that causes the motorised means to slide the lower arm out of the body portion when the switch is in a first position, and slidably retract the lower arm when the switch is in the opposite position.

In one preferred embodiment, the switch is a rocker switch.

Preferably, the switch is located on the extraoral portion of the body portion.

In another preferred embodiment, the switch is located on the pad assembly as a pair of momentary switches, one for retraction and one for extension.

In another preferred embodiment, the manual means also include a portable device such as a handheld computer, such as a smart phone, wherein said smart phone is wirelessly paired with the logic control means, and wherein the smart phone includes an app that includes manual control means that interact with the logic control means and is adapted to manually cause the motorised means to either extend of retract the lower arm.

Preferably, the portable device includes an app that records an optimal first position of the extraoral portion of the mandibular advancement device so that when subsequent mandibular advancement devices are paired to the portable device and linked to the specific account within the app, the app controls the optimal first position of that device that is best for that account holder.

Preferably, the portable device includes an app that links to an account belonging to the specific wearer of the device, and the account is adapted to receive telemetry from the logic control means, either in real-time, or in batch mode, and this telemetry is logged for that specific wearer within their account for subsequent analysis of breathing patterns and movement of the wearer's mandibular over a time period.

Optionally, the app includes alarm means that are enabled if/when the telemetry is lost from the mandibular advancement device.

Optionally, the app includes alarm means that are enabled if/when a fault within the adjustment means is detected by the logic control means, or if the battery powering the motorised means reaches a pre-set minimum charge.

According to another form, the present invention is a method of adjusting the position of the extraoral portion of a mandibular advancement device, including the steps of:

a) pairing a device to an account within an app on a portable device such as a smart phone; and
b) waiting for the extraoral device move into a first position under the control of the app; and
c) inserting the intraoral portion of the device within the oral cavity of the wearer; and
d) ensuring the mandibular advancement device is properly fitted so that the pad assembly makes proper contact with the subnasal maxillary bone of the wearer, and if necessary; and
e) using the manual adjustment means to fine tune the mandibular advancement device so that the mandible of the wearer is in its initial optimal position for both comfort and to provide the airflow sensors on pad assembly to sense an optimal based airflow for the wearer at the commencement of their use of the device; and
f) feeding the airflow sensor data in real-time to the logic control means; and
g) enabling the logic control means to analyse the sensor data to determine if the position of the mandible of the wearer should move, and if it is determined that the mandible should be moved; then
h) allowing the logic control means to operate the motorised means to either extend or retract the lower arm of the extraoral portion to thereby cause the pad assembly to either exert more or less force upon the subnasal maxillary bone of the wearer, thereby causing the mandible of the wearer to move to a new position.

DETAILED DESCRIPTION OF THE PREFERRED EMBODIMENTS

Figure 1:
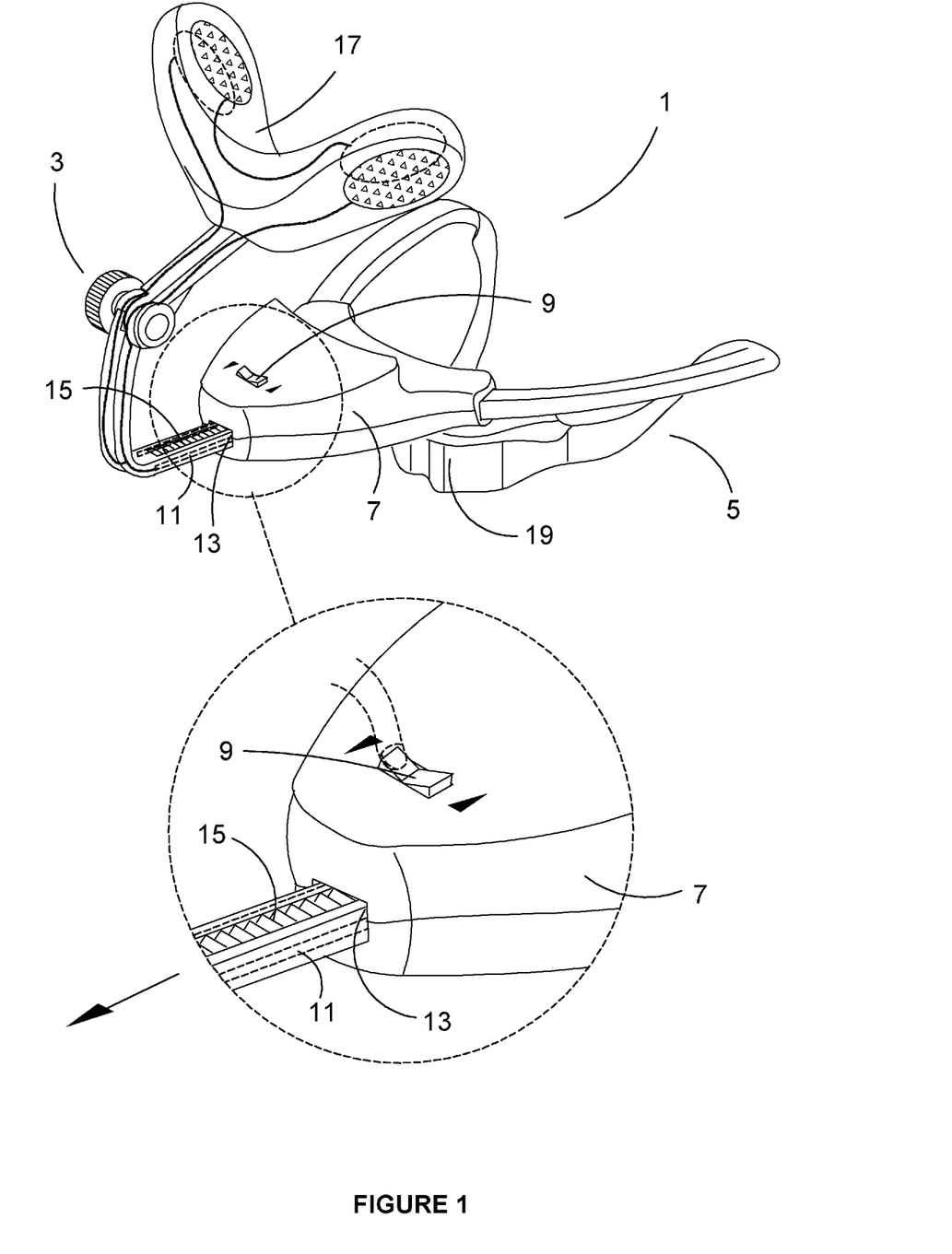
FIG. 1 is an isometric view of a mandibular advancement device showing one preferred form of the present invention.

Turning firstly to FIG. 1, where we are shown an isometric view of a mandibular advancement device 1. The device includes an extraoral portion 3 and extraoral portion 5. A body portion 7 is at the interface between the two portions and is therefore partly intraoral towards the posterior end and extraoral towards the anterior end. Electric motor means (not visible in this view) are encapsulated within the body portion 7. The extraoral portion 3 includes a lower straight arm 11 that is adapted to slide into or out of a corresponding opening 13 in the anterior end of the body portion 7. The straight arm 11 may include a rack 15 that engages with a pawl on the electric motor to cause the arm to move into or out of the body portion 7 as shown by the double ended arrow. A rocker switch 9 is formed in the extraoral portion of the body portion 7 and this is able to control the electric motor means. When the switch 9 is rocked in a first position, the motorised means act upon the lower arm 11 and forces it to move outwardly, and when the rocker switch 9 is rocked to a second position, the motorised means acts upon lower arm and forces it to move into the body portion. The upper portion of the extraoral portion 3 terminates at a pad assembly 17. When the mandibular advancement device 1 is worn, the pad assembly contacts the subnasal maxillary bone of the wearer. The upper pad assembly 17 braces against a lower pad 19 that is located on the intraoral portion 5 of the device 1 and contacts the gingiva and/or teeth of the wearer. The opposing forces applied by the pad assembly 17 and the lower pad 19 combine to adjust the position of the mandible of the wearer. By moving the extraoral portion 3 of the device 1, the operator of the rocker switch 9 thereby adjusts the force applied upon the subnasal maxillary bone of the wearer, and thereby causes a change in the position of the wearer's mandible.

Figure 2:
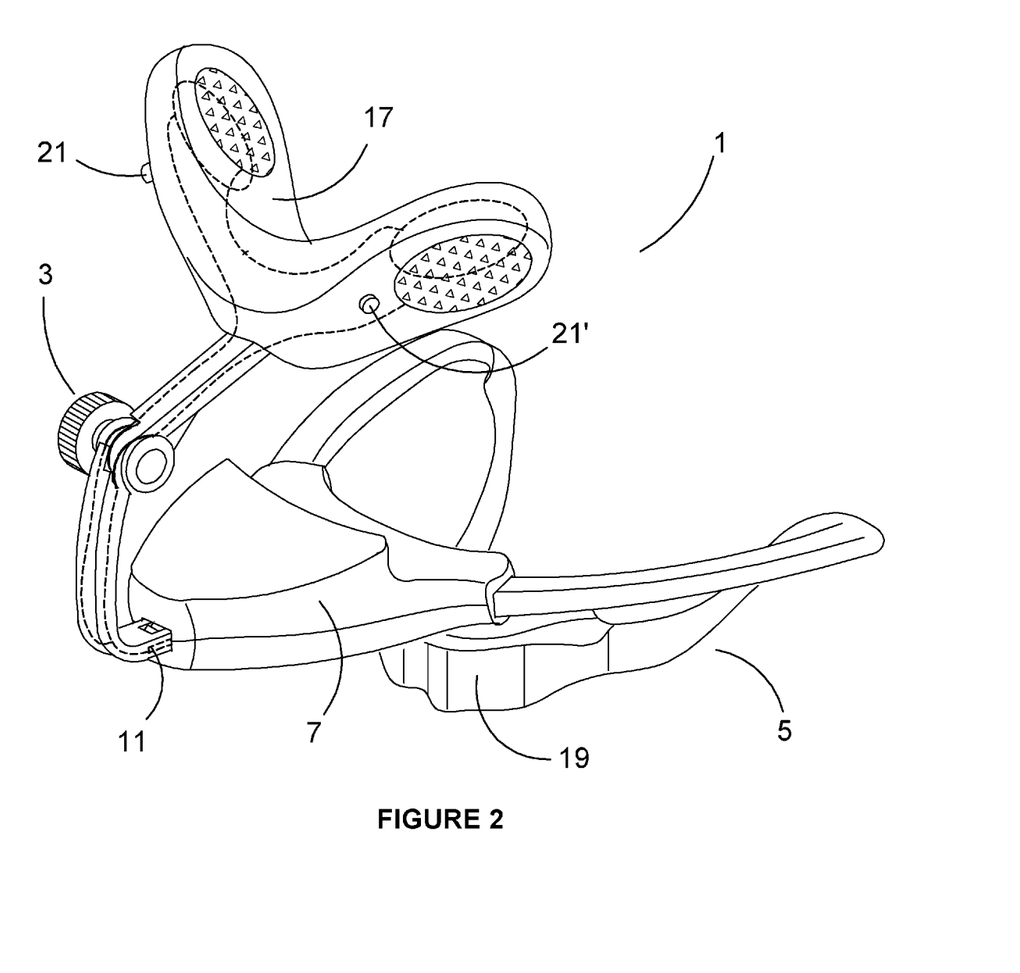
FIG. 2 shows an isometric view of a mandibular advancement device showing another preferred form of the present invention.

Now turning to FIG. 2, where we are shown an alternative embodiment of the present invention. In this embodiment, the rocker switch is removed from the body portion 7 and is relocated to the pad assembly 15 as a pair of monetary switches 21 and 21'. These momentary switches act similarly to the rocker switch 9 as shown in FIG. 1. When an operator, perhaps the wearer, depresses momentary switch 21, the electric motor encapsulated inside the body portion 7 is activated and causes the lower arm 11 to retract into the body portion 7, and when the operator depresses momentary switch 21', the electric motor is activated and causes the lower arm 11 to extend out from the body portion 7. The extraoral portion includes electrical wiring, preferably encapsulated within its body that enables the action of either momentary switch to activate the electric motor means within the body portion 7.

Figure 3:
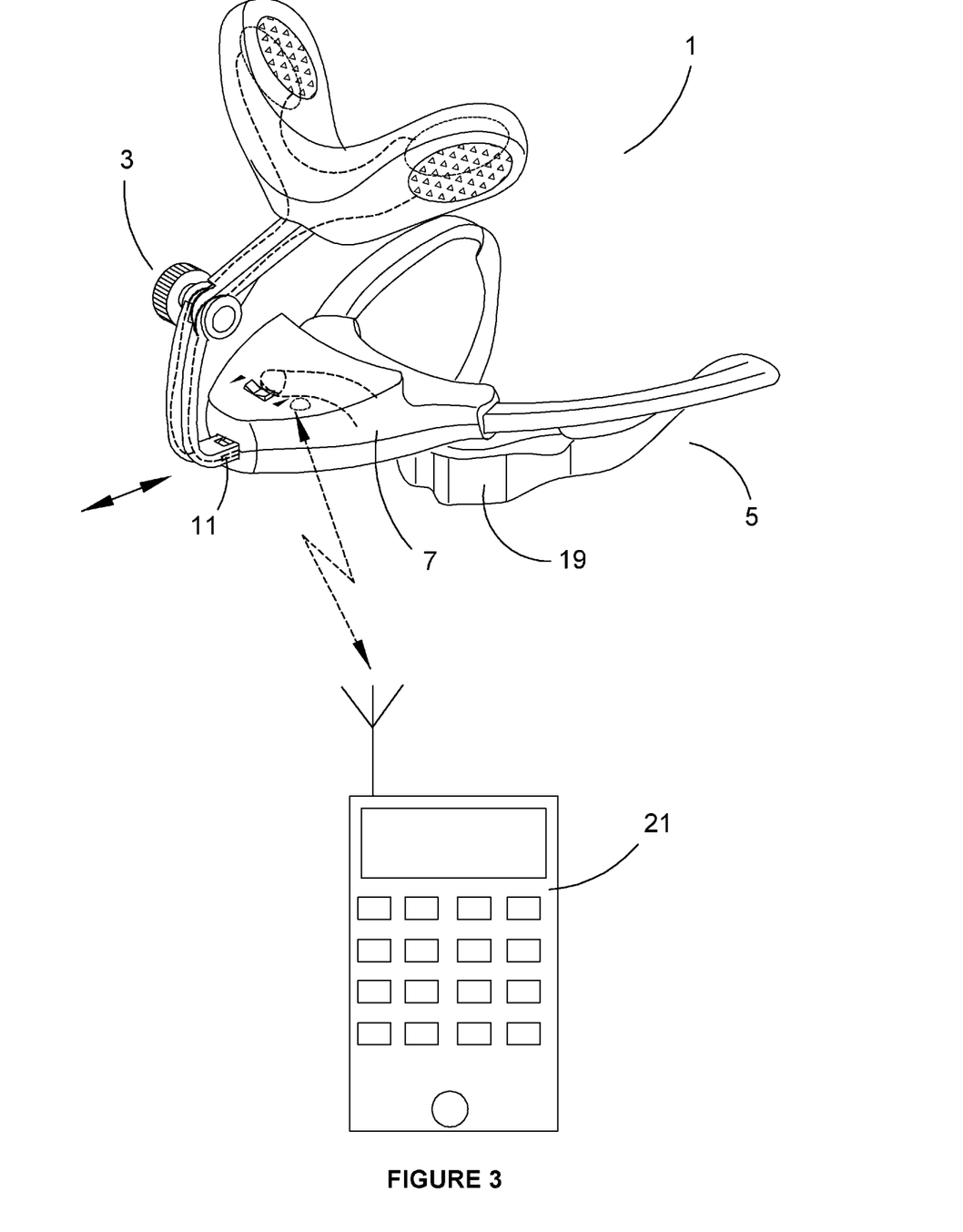
FIG. 3 shows an isometric view of a mandibular advancement device showing yet another preferred form of the present invention.

In FIG. 3 we are shown another preferred embodiment of the present invention. In this embodiment, all mechanical switches are removed from the device 1 and the electric motor means are instead controlled wirelessly. In this embodiment, the body portion 7 includes wireless transmission and receiving means that are adapted to pair with an external computerised device. In this example, a smart phone 21 is shown. The smart phone 21 includes an app that is designed to work with the device 1. In one mode of the app, the operator can use virtual buttons displayed on the smart phone's 21 screen to cause the electric motor means to move the lower arm 11 into or out of the body portion 7.

Figure 4:
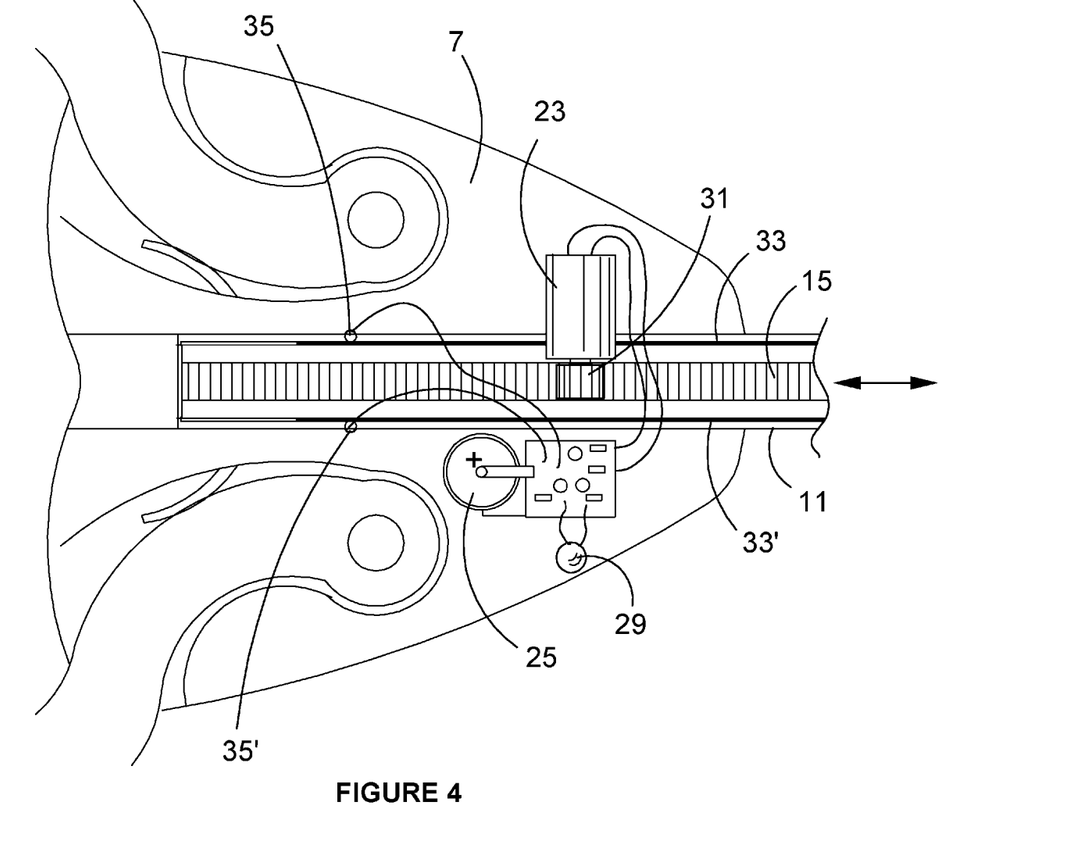
FIG. 4 shows a plan view of a preferred form of the invention and shows the electric motor means of adjusting the extraoral portion.

In FIG. 4, we are shown a plan view of the body portion 7 in accordance with one embodiment of the present invention. In this view we can see the electric motor 23 mounted inside the lower half of the body portion 7. The electric motor 23 is powered by rechargeable battery 25. Optionally, the invention may also include logic control means 27. The logic control means may be programmed to provide automatic functionality of the device 1. Wireless connectivity may also be included. The body portion 7 may also include a wireless antenna 29 that enables the device 1 to wirelessly connect to an external computerised device. As shown in this view, the electric motor 23 is fitted with a pawl 31 that engages with the rack 15 on the lower arm 11. Of course, other arrangements for engagement between the electric motor 23 and the lower arm 11 are possible and fit within the scope of this invention. Also shown in this view is one preferred option using electrical rails 33 and 33' for transmitting electrical signals when momentary switches are included upon the pad assembly. The electrical rails 33 and 33' are electrically connected to the slide contacts 35 and 35'

Figure 5:
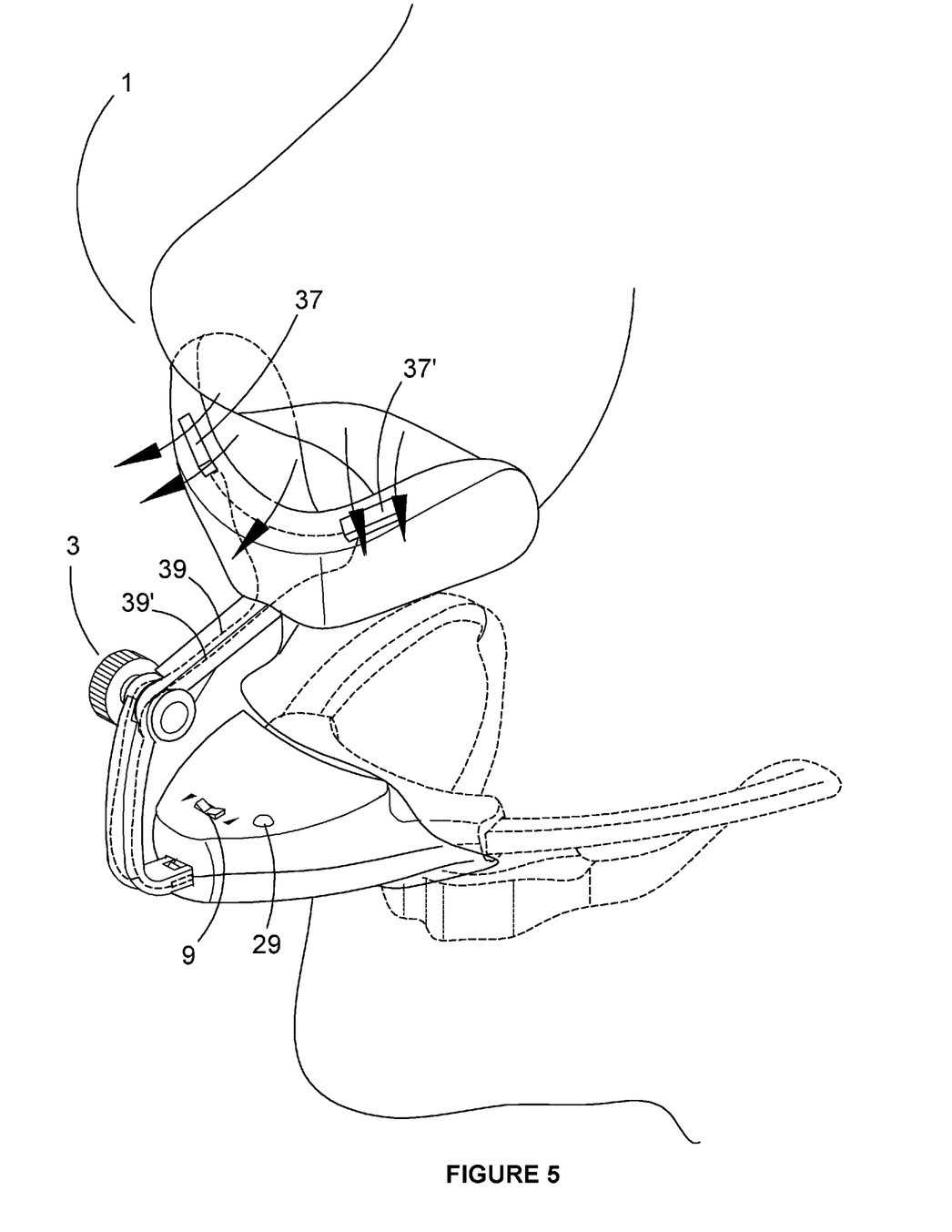
FIG. 5 shows an isometric view of a mandibular advancement device showing yet another preferred form of the present invention.

In FIG. 5, we are shown another embodiment of the present invention. In this embodiment, two airflow sensors 37 and 37' are located directly below the nostrils of the wearer of the device. As the wearer breathes, the sensors 37 and 37' determine the airflow rate. This data is then fed to the logic control means via wires 39 and 39'. The logic control means are programmed to analyse the airflow data. If the logic control means determine that the flowrate associated with the wearer's breathing has changed sufficiently, then the logic control means are programmed to autonomously engage the electric motor means and adjust the position of the wearer's mandible in an attempt to affect the wearer's breathing and return the rate of airflow back within a set of control limits. The logic control means may also send telemetry wirelessly to an external computerised device. This can be done continuously or in batches. This arrangement makes the device 1 completely automatic. Once the nominal breathing rate is determined, and the maximum and minimum control points set, then the device will automatically alter the position of the wearer's mandible in an autonomous attempt to correct undesirable changes in breathing. The telemetry sent to the external computerised device is capable of giving the wearer and other careers and health service professionals valuable insights into the wearer's breathing patterns while using the device.

The device may also include a manual override, as shown in this example as rocker switch 9 so that a wearer can take manual control of the device. A slider switch may be included on either the body, or the pad assembly that enables a wearer or care giver to switch off the automatic mode of operation.

While the above description includes the preferred embodiments of the invention, it is to be understood that many variations, alterations, modifications and/or additions may be introduced into the constructions and arrangements of parts previously described without departing from the essential features or the spirit or ambit of the invention.

It will be also understood that where the word "comprise", and variations such as "comprises" and "comprising", are used in this specification, unless the context requires otherwise such use is intended to imply the inclusion of a stated feature or features but is not to be taken as excluding the presence of other feature or features.

The reference to any prior art in this specification is not, and should not be taken as, an acknowledgment or any form of suggestion that such prior art forms part of the common general knowledge.

The invention claimed is:

1. A mandibular advancement device having both intraoral and extraoral portions; and an adjustment means, wherein:
    the adjustment means includes a body portion that is at an interface between the intraoral and extraoral portions, thereby being part intraoral and part extraoral when in use; and
    the extraoral portion includes a lower arm that is straight and extends directly outwardly from the extraoral part of the body portion, and a curved upper arm-that curves upwardly from the lower arm and back towards a face of a wearer of the device when the device is in use, a posterior end of the upper arm including a pad assembly that is adapted to make contact with, and apply pressure to, a subnasal maxillary bone of the wearer,
    wherein the body portion includes motorised means encapsulated within the body portion, a portion of the lower arm being engageable with the motorised means, the motorised means being adapted to engage with the lower arm and cause it to slidably extend from, or slidably retract into, the body portion, and
    wherein the pad assembly includes sensor means that are adapted to sense airflow emanating from a nose of the wearer as they breathe while wearing the device and feed sensor data collected in real time to logic control means contained within the body portion via wires extending along the lower and upper arms, and
    wherein the logic control means are adapted to process the sensor data received to determine if a position of a mandible of the wearer needs adjusting to improve airflow from the wearer, and if so, then the logic control means are adapted to activate the motorised means to either extend or retract the lower arm for an appropriate distance, thereby causing the pad assembly to apply more or less pressure to the subnasal maxillary bone, and thereby change the position of the mandible of the wearer into a new position.

2. The mandibular advancement device as defined in claim 1 including a manual means adapted to enable the wearer to manually control the motorised means so that the wearer can set a first desired position for the extraoral portion of the device.

3. The mandibular advancement device as defined in claim 2 wherein the manual means includes a portable device, wherein said portable device is wirelessly paired with the logic control means, and wherein the portable device includes an app that includes manual control means that is adapted to interact with the logic control means and to manually cause the motorised means to either extend or retract the lower arm.

4. The mandibular advancement device as defined in claim 3 wherein the app is adapted to enable the wearer of the device to create an account within the app, the app recording an optimal first position of the extraoral portion of the mandibular advancement device so that when subsequent mandibular advancement devices are paired to the portable device and linked to the account within the app, the app controls the optimal first position of a respective subsequent mandibular advancement device.

5. The mandibular advancement device as defined in claim 4 wherein the app is adapted to link to the account belonging to the wearer of the device, and the account belonging to the wearer of the device is adapted to receive telemetry from the logic control means, either in real-time, or in batch mode, and this telemetry is logged for the wearer within their account for subsequent analysis of breathing patterns and movement of the wearer's mandible over a time period.

6. The mandibular advancement device as defined in claim 5 wherein the app includes alarm means that are enabled if/when the telemetry is lost from the mandibular advancement device.

7. The mandibular advancement device as defined in claim 4 wherein the app includes alarm means that are enabled if/when a fault within the adjustment means is detected by the logic control means, or if a battery powering the motorised means reaches a pre-set minimum charge.

8. The mandibular advancement device as defined in claim 2 wherein the manual means includes a switch that is adapted to cause the motorised means to slidably extend the lower arm from the body portion when the switch is in a first position, and slidably retract the lower arm into the body portion when the switch is in an opposite position.

9. The mandibular advancement device as defined in claim 8 wherein the switch is a rocker switch.

10. The mandibular advancement device as defined in claim 8 wherein the switch is located on the extraoral portion of the body portion.

11. The mandibular advancement device as defined in claim 8 wherein the switch is located on the pad assembly as a pair of momentary switches, one for retraction and one for extension.

12. A method of adjusting a position of an extraoral portion of a mandibular advancement device as defined in claim 1, the method including the steps of:
 a) pairing the device to an account within an app on a portable device; and
 b) waiting for the extraoral portion to move into a first position under control of the app; and
 c) inserting the intraoral portion of the device within an oral cavity of the wearer; and
 d) ensuring the pad assembly is fitted to contact the subnasal maxillary bone of the wearer, and
 e) using a manual adjustment means of the device to fine tune the device so that the mandible of the wearer is in an initial optimal position for both comfort and to provide the sensor means on the pad assembly to sense an optimal base airflow for the wearer at commencement of use of the device; and
 f) feeding the sensor data in real-time to the logic control means; and
 g) enabling the logic control means to analyse the sensor data to determine if the position of the mandible of the wearer should move, and if it is determined that the mandible should be moved; then
 h) allowing the logic control means to operate the motorised means to either extend or retract the lower arm of the extraoral portion to thereby cause the pad assembly to either exert more or less force upon the subnasal maxillary bone of the wearer, thereby causing the mandible of the wearer to move to the new position.

* * * * *

UNITED STATES PATENT AND TRADEMARK OFFICE
CERTIFICATE OF CORRECTION

| | | |
|---|---|---|
| PATENT NO. | : 12,383,420 B2 | Page 1 of 1 |
| APPLICATION NO. | : 17/638691 | |
| DATED | : August 12, 2025 | |
| INVENTOR(S) | : Owen Morgan and Anthony Sasse | |

It is certified that error appears in the above-identified patent and that said Letters Patent is hereby corrected as shown below:

In the Claims

Column 5, Line 48, in Claim 1, delete "portions;" and insert --portions--.

Column 5, Line 56, in Claim 1, delete "arm-that" and insert --arm that--.

Column 6, Line 28, in Claim 3, before "manually" delete "to".

Signed and Sealed this
Seventh Day of October, 2025

John A. Squires
*Director of the United States Patent and Trademark Office*